United States Patent [19]

Yamanishi et al.

[11] Patent Number: 4,837,331

[45] Date of Patent: Jun. 6, 1989

[54] STABILIZATION OF TETRAZOLIUM SALTS WITH CYCLODEXTRINS

[75] Inventors: Kazuhiko Yamanishi, Tokyo; Toshiro Hanada, Kawagoe, both of Japan

[73] Assignee: Wako-Pure Chemical Industries, Ltd., Osaka, Japan

[21] Appl. No.: 930,094

[22] Filed: Nov. 13, 1986

[30] Foreign Application Priority Data

May 30, 1983 [JP] Japan .................................. 95185/83

[51] Int. Cl.$^4$ .................. C07D 257/04; C07D 403/12; C07D 417/04
[52] U.S. Cl. .................................. 548/146; 548/250; 548/252; 548/254; 530/46; 530/103
[58] Field of Search ............... 548/250, 146, 252, 254; 536/46

[56] References Cited

U.S. PATENT DOCUMENTS 3,954,787  5/1976  Monkhouse ........................ 424/269

OTHER PUBLICATIONS

Tsou et al., J. Am. Chem. Soc, 78, pp. 6139–6144 (1956).
Nineham, "Chemical Reviews", 55 (1955), pp. 355 and 423.

*Primary Examiner*—David B. Springer
*Attorney, Agent, or Firm*—Armstrong, Nikaido, Marmelstein, Kubovcik & Murray

[57] ABSTRACT

An aqueous solution containing a tetrazolium compound used for determining superoxide ions can be stabilized by adding β-cyclodextrin and/or a derivative thereof and/or γ-cyclodextrin.

6 Claims, No Drawings

STABILIZATION OF TETRAZOLIUM SALTS WITH CYCLODEXTRINS

This application is a continuation of application Ser. No. 615,028 filed May 30, 1984.

This invention relates to a process for stabilizing a tetrazolium compound using cyclodextrin as an effective component.

Tetrazolium compounds such as nitrotetrazolium blue (hereinafter referred to as "$NO_2$-TB") are generally low in oxidation-reduction potential and when they are reduced, there are produced formazan compounds such as monoformazan compounds or diformazane compounds which exhibit an orange to blue color. Therefore, they are widely used as reagent for colorimetrically measuring dehydrogenases or as reagent for colorimetrical determination of reductive substances such as reduced type coenzymes, superoxide irons, etc., in the fields of clinical chemistry, pharmaceutical chemistry, biochemistry, food chemistry, and the like. For example, there is known a process for measuring components in a body fluid sample using a tetrazolium compound wherein superoxide ions ($O_2^-$) produced quantitatively by a reaction reduce the tetrazolium compound quantitatively to produce a formazan compound, the color of which is measured quantitatively (European Patent Publication No. 010027A2).

As an example of the reaction for producing such superoxide ions, there is known an enzymatic reaction wherein superoxide ions are produced by acting an oxidase on a substrate. In order to conduct such an enzymatic reaction practically, an oxidase is acted on a substrate preferably in the presence of a thiol compound, peroxidase or an iron complex of porphyrin or an iron chelate compound of complexane, an amine or a phenol, and preferably together with a chelating agent, to produce superoxide ions, which are used for determination of the desired components. When superoxide ions can stably be produced as they are as in the case of acting xanthine oxidase on xanthine, the presence of such reagents as mentioned above is not required.

For example, cholesterol can be determined by using such a principle as follows:

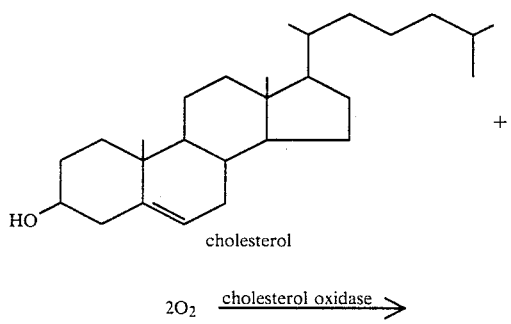
cholesterol $2O_2$ $\xrightarrow{\text{cholesterol oxidase}}$

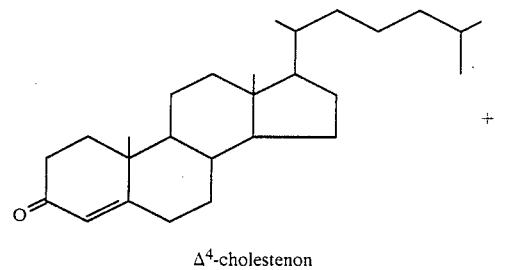
$\Delta^4$-cholestenon $2O_2^- + 2H^+$

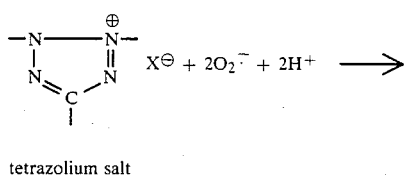 $X^\ominus + 2O_2^- + 2H^+ \longrightarrow$ tetrazolium salt

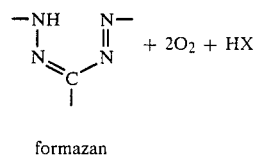 $+ 2O_2 + HX$ formazan

Since the above-mentioned reactions proceed quantitatively and specifically, the amount of cholesterol can be determined by measuring the color intensity of the formazan produced. (In the above-mentioned formulae, "X" represents a halogen.)

Generally speaking, an aqueous solution of a tetrazolium compound is not sufficiently stable, and becomes unstable when exposed to light, or kept in neutral or alkaline conditions, or by the presence of an interfering substance. For example, when there is present a reductive substance such as a thiol compound, the tetrazolium compound is gradually decomposed to produce a color, which results in raising reagent blank values with the lapse of time and causing errors in the measurement. Therefore, in the case of quantitatively measuring the color of formazan compound produced quantitatively by the reduction of tetrazolium compound with superoxide ions, the tetrazolium compound becomes unstable when exposed to light, or kept in neutral or alkaline conditions, or by the presence of a thiol compound and the solution containing the thiol compound and tetrazolium compound is colored to damage the quantitative measurement of the desired component.

It is an object of this invention to overcome the problem of the prior art process and to provide a process for stabilizing a tetrazolium compound in an aqueous solution.

This invention provides a process for stabilizing a tetrazolium compound in an aqueous solution which comprises adding at least one member selected from the group consisting of β-cyclodextrin, a derivative thereof and γ-cyclodextrin to the aqueous solution, said tetrazolium compound having a moiety of the formula:

 (I)

In this invention, at least one member selected from the group consisting of β-cyclodextrin, a derivative thereof and γ-cyclodextrin should be used for stabilizing the tetrazolium compound having the moiety of the formula (I). In contrast, α-cyclodextrin has no effect for stabilizing the tetrazolium compound having the moiety of the formula (I). This seems to be that both β-cyclodextrin, or a derivative thereof and γ-cyclodextrin have a clathrate action for the tetrazolium compound, while α-cyclodextrin has no such a clathrate action.

The tetrazolium compound thus stabilized by β-cyclodextrin, and/or a derivative of β-cyclodextrin, and/or γ-cyclodextrin can be reduced by superoxide ions with sufficiently fast reaction rate to produce a formazan compound, the color of which is measured for determining the amount of superoxide ions with sufficient sensitivity. There is no influence of the addition of β-cyclodextrin, and/or a derivative of β-cyclodextrin, and/or γ-cyclodextrin to the tetrazolium compound on the color development rate and the increase in reagent blank value can be suppressed decisively.

The tetrazolium compound usable in this invention is those having the moiety of the formula (I).

Examples of such tetrazolium compounds are monotetrazolium compounds having the formula:

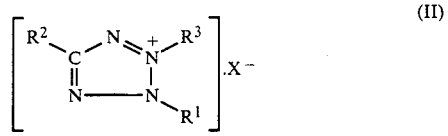

(II)

wherein X is a halogen; and $R^1$, $R^2$, and $R^3$ are independently organic residues such as a phenyl group, a phenyl group substituted by one or more halogens such as iodine, or nitro group, a group of the formula:

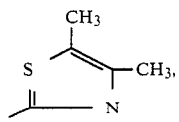

etc. Typical examples of monotetrazolium compounds having the formula (II) are as follows:

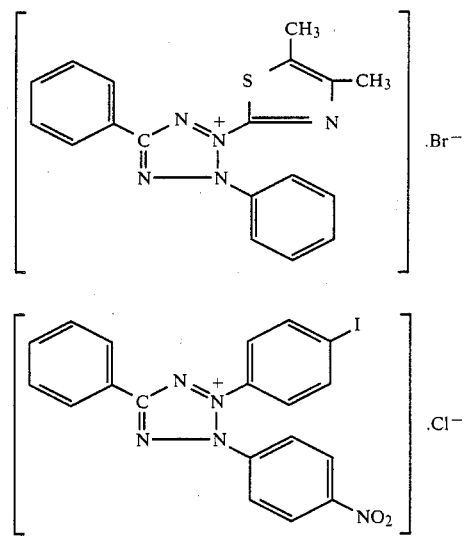

It is also possible to use ditetrazolium compounds of the following formula as the tetrazolium compound having the moiety of the formula (I):

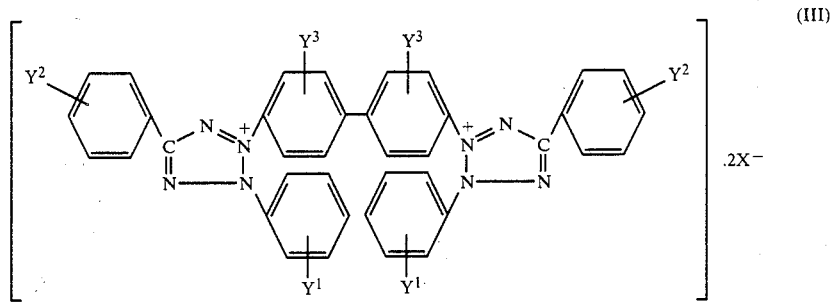

(III)

wherein $Y^1$ and $Y^2$ are independently —$NO_2$ or —H; $Y^3$ is —$OCH_3$, —I or —H; and X is a halogen. Typical examples of ditetrazolium compounds of the formula (III) are as follows:

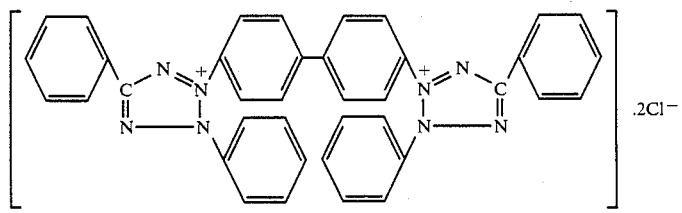

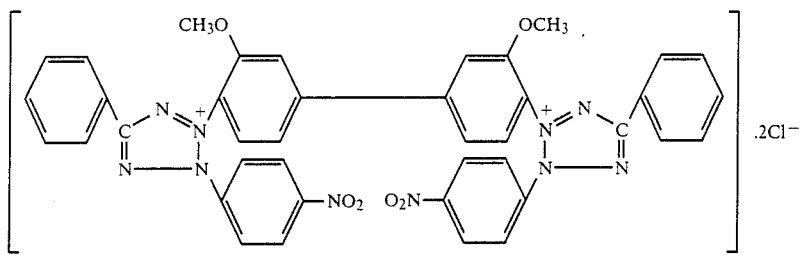

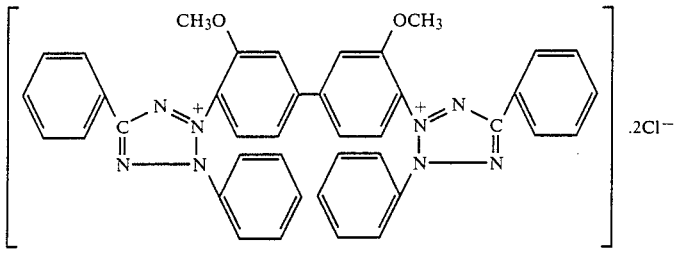

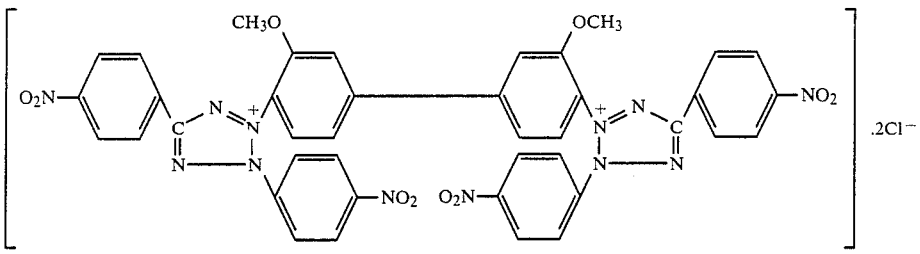

As is well known, these tetrazolium compounds are reduced to form corresponding formazan compounds having specific colors which are used for colorimetrical determination.

On the other hand, it is generally known that formazan compounds produced by reducing tetrazolium compounds have strong staining properties for vessels made from such materials as glass, plastics, etc. For example, a cuvette used for measuring absorbance is often stained strongly to cause errors. Such a problem of staining vessels can be solved by using gelatin as an effective component. Gelatin can effectively inhibit staining power of the formazan compounds produced from tetrazolium compounds. That is, when gelatin is present in an aqueous solution containing a tetrazolium compound, staining caused by a formazan compound which is a reduction product of the tetrazolium compound can effectively be prevented.

The problem of staining vessels can also be solved by making the formazan compound which is a reduction product of a tetrazolium compound water-soluble. Examples of tetrazolium compounds which can form water-soluble formazan are those represented by the formula:

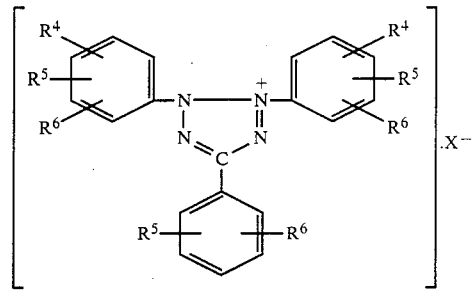

wherein $R^4$ is a nitro group or hydrogen, but at least one $R^4$ should be a nitro group; $R^5$ is hydrogen, a lower alkyl group, a lower alkoxy group or a halogen; $R^6$ is hydrogen or $-OR^7$; $R^7$ is a straight- or branched-chain aliphatic hydrocarbon having 1 to 4 carbon atoms which has at least one sulfonic acid group or sulfonic acid salt group and/or carboxyl group or carboxyl salt group and can also have a hydroxyl group, provided that the number of sulfonic acid (or its salt) group or carboxyl (or its salt) group contained in $R^6$ is 2 or more as a total and one of them forms an intramolecular salt with a tetrazolium ring; and X is a halogen. Examples of tetrazolium compounds of the formula (IV) are 2-(nitrophenyl)-3,5-di(sulfopropoxyphenyl)-2H-tetrazolium salts, etc. These tetrazolium compounds which can form water-soluble formazan compounds can be used in an amount of 1 to 40 mg/dl in the reaction solution at the time of color development irrespective of their water solubility.

The concentration of β-cyclodextrin or a derivative thereof or γ-cyclodextrin for stabilizing the tetrazolium compound in the aqueous solution is usually 0.01 to 1.5 weight/volume percent, preferably 0.1 to 0.5 weight-/volume percent, in the case of β-cyclodextrin, usually 0.01 to 10 weight/volume percent, preferably 0.1 to 5 weight/volume percent in the case of a derivative of β-cyclodextrin, and usually 0.01 to 10 weight/volume percent, preferably 0.1 to 3 weight/volume percent, in the case of γ-cyclodextrin. β-Cyclodextrin or a derivative thereof and γ-cyclodextrin can be used as a mixture thereof in any ratio within the above-mentioned range of individual concentrations.

The derivative of β-cyclodextrin can be represented by the formula:

$$\beta\text{-CD}(-OH)_{21-m}(-OZ^1)_m \quad (V)$$

wherein CD is a cyclodextrin residue; $Z^1$ is $-NO_2$, $-PO_3H$, $-SO_3H$ or a group of the formula: $-(CH_2)_nZ^2$; $Z^2$ is $-SO_3H$ or $-CO_2H$; n is an integer of 1 to 4; and m is a value of 1 to 5, or represented by the formula:

$$\beta\text{-CD}(-OH)_{21-k}(-OCH_3)_k \quad (VI)$$

wherein $0 < k \leq 21$.

Examples of the derivatives of β-cyclodextrin are as follows:
β-CD(—OH)$_{19}$(—ONO$_2$)$_2$
β-CD(—OH)$_{19.2}$(—OPO$_3$H)$_{1.8}$
β-CD(—OH)$_{19}$(—OSO$_3$H)$_2$
β-CD(—OH)$_{18.5}$(—O—CH$_2$—CO$_2$H)$_{2.5}$
β-CD(—OH)$_{19.3}$(—O—CH$_2$CH$_2$CH$_2$—SO$_3$H)$_{1.7}$
β-CD(—OH)$_{18.5}$(—O—CH$_2$CH$_2$CH$_2$—SO$_3$H)$_{2.5}$
β-CD(—OH)$_{18.0}$(—O—CH$_2$CH$_2$CH$_2$—SO$_3$H)$_{3.0}$
β-CD(—OH)$_7$(—OCH$_3$)$_{14}$
β-CD(—OCH$_3$)$_{21}$ Needless to say, the examples of the derivatives of β-cyclodextrin are not limited thereto.

There derivatives of β-cyclodextrin can easily be prepared by a conventional method.

The gelatin used for effectively inhibiting staining by the formazan compound produced by reducing the tetrazolium compound preferably has an average molecular weight of 20,000 to 150,000. Water-soluble gelatin having an average molecular weight of 1000 to 2000 usually does not show a particular effect for inhibiting the staining by formazan compound. But any gelatin having an inhibiting effect of staining can be used. For example, gelatin derived from animal bones and animal skins is available commercially, and any other gelatin can also be used. The gelatin concentration in the aqueous solution effective for preventing staining is usually 0.1 to 0.7 weight/volume percent, preferably 0.2 to 0.5 weight/volume percent.

As mentioned above, since the tetrazolium compound which is a color producing reagent to be reduced can be stabilized in an aqueous solution even if a thiol compound is present or exposed to light or under neutral or alkaline conditions and the staining by formazan compound can be prevented, this invention can be applied to determination of substrates, for example, in body fluid samples in clinical chemical examinations wherein a thiol compound is usually used for producing superoxide ions to be determined. In such a case, a reagent composition comprising (a) an oxidaze, (b) a peroxidase, or an iron complex of porphyrin or an iron chelate compound of complexane, (c) a phenol and/or an amine, (d) a thiol compound, (e) a tetrazolium compound which is a color producing reagent to be reduced, and if required (f) a chelating agent can be used.

Examples of the thiol compound are reduced from glutathione, thioglycolic acid, mercaptoethanol, thiosalicylic acid, cysteamine, cysteine, dimercaptosuccinic acid, etc. It is also possible to use coenzymes having a SH group therein such as CoA. The thiol compound can be used in an amount of about 1 to 50 mg/dl in the reaction solution at the stage of color development.

As the amine, there can be used conventional organic amines. Aromatic amines are more effective than aliphatic amines with a small using amount. There can be used primary amines, secondary amines and tertiary amines. Examples of these amines are aniline, N-ethylaniline, N,N-dimethylaniline, N,N-diethyl-m-toluidine, N-ethyl-N-β-hydroxyethyl-m-toluidine, 3,5-dimethoxy-N-ethyl-N-(2-hydroxy-3-sodiumsulfopropyl)aniline, etc. The amine can be used in an amount of about 0.0001% to 0.2% by weight in the reaction solution at the stage of color development.

The phenol is not particularly influenced by other substituents. As the phenol, there can be used phenol, chlorophenols, dichlorophenols, naphthol sulforic acid derivatives and the like. The phenol can be used in an amount of about 0.0001% to 0.2% by weight in the reaction solution at the stage of color formation.

A phenol and an amine can be used together.

The peroxidase can be used in an amount of about 50 to 1000 units/dl in the reaction solution at the stage of color development.

As the iron complex of porphyrin used in place of peroxidase, there can be used hemin, α,β,γ,δ-tetraphenylporphyrintrisulfonic acid-iron complex, α,β,γ,δ-tetrakis(4-N-methylpyridyl)-porphyrin-iron complex, tetraphenylporphyrin-iron complex, octaethylporphyrin-iron complex, etc. The iron complex of porphyrin can used in an amount of about 0.007 to 0.06 mmol/l in the reaction solution at the stage of color development.

As the iron chelate of complexane used in place of peroxidase, there can be used iron chelated of complexanes such as ethylenediaminetetraacetic acid (EDTA), diaminopropanetetraacetic acid, trans-cyclohexanediaminetetraacetic acid, hydroxyethylethylenediaminetriacetic acid, glycol ether diaminetetraacetic acid, etc. The iron chelate of complexane can be used in an amount of about 0.01 to 0.07 mmole/l. in the reaction solution at the stage of color development.

As the chelating agent which is used for preventing autooxidation of additives such as a thiol compound, and for proceeding the reaction stably, there can be used ethylenediaminetetraacetic acid (EDTA), trans-cyclohexanediaminetetraacetic acid=trans-1,2-cyclohexanediamine-N,N,N',N'-tetraacetic acid (CyDTA), diethylenetriaminepentaacetic acid=diethylenetriamine-N,N,N',N'',N''-pentaacetic acid (DTPA), etc. The chelating agent can be used in an amount of about 0.5 to 5 mmole/dl in the reaction solution at the stage of color development.

In the case of using the above-mentioned compounds in proper combination, if the final mixture to be measured on its coloring is clouded to damage the measurement, a surface active agent or solubility aid can be added thereto according to a conventional process.

Oxidases are enzymes which specifically oxidize substrates in enzymatic reactions. Substrates and corresponding specific oxidases usable in this invention can be listed as follows:

Glucose
Glucose oxidase
Cholesterol
Cholesterol oxidase
Glycerol
Glycerol oxidase
Glycerolphosphate
Glycerolphosphate oxidase
Choline
Choline oxidase
Acyl CoA
Acyl CoA oxidase
Pyruvic acid
Pyruvate oxidase
Uric acid
Uricase
Xanthine
Xanthine oxidase
Lactic acid
Lactate oxidase Enzymatic reactions mentioned above can be applied to measuring the amounts of substrates in body fluid (samples) or measuring the activities of serum enzymes. Examples of compositions of reagents used for such measuring are listed below:

Determination of cholesterol:

| | |
|---|---|
| Cholesterol oxidase | 10–50 units/dl |
| $NO_2$—TB | 10–30 mg/dl |
| β-cyclodextrin | 0.1–0.5% |
| gelatin | 0.1–0.5% |
| reduced form glutathione | 0.01–0.1% |
| a phenol or an amine | 0.005–0.5% |
| peroxidase | 100–1000 units/dl |
| or hemin | 0.0005–0.002% |
| chelating agent | 0.0005–0.002% |
| Triton X-100* | 0.05–0.2% |
| 0.05–0.2 M tris or phosphate buffer | pH 7.5–8.5 |

*Octylphenoxy polyethoxyethanol-available from Rohm and Haas Company.

Determination of free fatty acid:

| | |
|---|---|
| acyl CoA synthetase | 5–30 units/dl |
| acyl CoA Oxidase | 100–6000 units/dl |
| adenosine-5'-triphosphate disodium salt (ATP) | 10–100 mg/dl |
| CoA | 20–50 mg/dl |
| magnesium chloride | 0.5–3 mmole/l |
| $NO_2$—TB | 10–30 mg/dl |
| β-cyclodextrin | 0.1–0.5% |
| gelatin | 0.1–0.5% |
| peroxidase | 100–1000 units/dl |
| a phenol or an amine | 0.005–0.5% |
| chelating agent | 0.0005–0.002% |
| Triton X-100 | 0.05–0.5% |
| buffer solution | pH 7.0 |

Determination of phospholipid:

| | |
|---|---|
| phospholipase D | 40–100 units/dl |
| choline oxidase | 150–500 units/dl |
| $CaCl_2.2H_2O$ | 3–10 mg/dl |
| β-cyclodextrin | 0.1–0.5% |
| gelatin | 0.1–0.5% |
| $NO_2$—TB | 10–30 mg/dl |
| peroxidase | 100–1000 units/dl |
| reduced form glutathione | 0.01–0.1% |
| a phenol or an amine | 0.005–0.5% |
| chelating agent | 0.0005–0.002% |
| Triton X-100 | 0.05–0.5% |
| buffer solution | pH 8.0 |

Determination of triglyceride:

| | |
|---|---|
| lipoprotein lipase | 3000–6000 units/dl |
| glycerol kinase | 150–500 units/dl |
| glycerol-3-phosphate oxidase | 100–400 units/dl |
| ATP | 100–300 mg/dl |
| magnesium acetate | 3–10 mmole/l |
| β-cyclodextrin | 0.1–0.5% |
| gelatin | 0.1–0.5% |
| $NO_2$—TB | 10–30 mg/dl |
| peroxidase | 100–1000 units/dl |
| reduced form glutathione | 0.01–0.1% |
| a phenol or an amine | 0.005–0.5% |
| chelating agent | 0.0005–0.002% |
| Triton X-405* | 0.01–0.3% |
| buffer solution | pH 7.0 |

*Alkylphenoxy polyethoxythanol-available from Rohm and Haas Company.

According to this invention, a tetrazolium compound in an aqueous solution can be stabilized by adding β-cyclodextrin and/or a derivative thereof and/or γ-cyclodextrin as an effective component to the aqueous solution. Particularly when a thiol compound is present in the aqueous solution wherein a substrate is acted with an oxidase to produce superoxide ions ($O_2^-$), the tetrazolium compound becomes unstable by the presence of the thiol compound; but such an unstabilizing phenomenon can effectively be prevented by the action of β-cyclodextrin and/or a derivative thereof and/or γ-cyclodextrin without causing any undesirable influences on the colorimetrical determination. Thus, when a desired component in a sample (e.g. a body fluid) is to be determine by applying the present invention, the increase in reagent blank values can be suppressed effectively due to the stabilization of tetrazolium compound. Therefore the present invention can widely be applied to clinical chemistry, pharmaceutical chemistry, biochemistry, food chemistry and the like, wherein the colorimetrical determination of the formazan compound which is produced by reducing a tetrazolium compound is used.

This invention is illustrated by way of the following Examples.

EXAMPLE 1

Determination of Free Cholesterol in Serum

A color producing reagent was prepared by using the following ingredients:

| | |
|---|---|
| $NO_2$—TB | 20 mg/dl |
| phenol | 0.01% |
| Triton X-100 | 0.1% |
| peroxidase (available from Toyobo Co., Ltd.) | 300 units/dl |
| cholesterol oxidase (available from Amano Pharmaceutical Co., Ltd.) | 15 units/dl |
| glutathione (reduced form) | 20 mg/dl |
| gelatin | 0.5% |
| β-cyclodextrin | 0.2% |
| 0.1 M tris buffer | pH 8.0 |

Measurement of Free Cholesterol in Serum

To 50 μl of serum, 3 ml of the color producing reagent was added and incubated at 37° C. for 10 minutes. Then, absorbance at the wavelength of 560 nm was measured by using water as control. On the other hand, absorbance of deionized water in place of serum treated in the same manner as mentioned above was also measured as reagent blank.

Further, absorbance of an isopropanol solution containing cholesterol in an amount of 200 mg/dl (standard solution) was also measured in the same manner as mentioned above.

The free cholesterol concentration in the serum was calculated by the following equation:

$$\frac{E_S - E_B}{E_{std} - E_B} \times 200 \text{ mg/dl}$$

wherein
$E_S$: absorbance when the serum was used
$E_B$: reagent blank value
$E_{std}$: absorbance when the standard solution was used.

COMPARATIVE EXAMPLE 1

Determination of Free Cholesterol in Serum

A color producing reagent was prepared in the same manner as mentioned in Example 1 except for not using gelatin and β-cyclodextrin.

Measurement of Free Cholesterol in Serum

The procedures of Example 1 were repeated.
The result of measured values are shown in Table 1.

TABLE 1

| Serum No. | Reagent | |
|---|---|---|
| | Example 1 (mg/dl) (Y) | Comparative Example 1 (mg/dl) (X) |
| 1 | 44.3 | 43.9 |
| 2 | 32.5 | 32.8 |
| 3 | 66.8 | 66.5 |
| 4 | 44.0 | 44.0 |
| 5 | 59.8 | 59.5 |
| 6 | 48.9 | 49.0 |
| 7 | 35.5 | 36.0 |
| 8 | 40.2 | 40.0 |
| 9 | 39.3 | 39.4 |
| 10 | 47.7 | 47.4 |
| Average | 45.90 | 45.85 |

$\gamma = 1.000$
$Y = 1.02 X - 0.79$

Comparison of reagent blank values is shown in Table 2.

TABLE 2

| Example No. | Example 1 | Comparative Example 1 |
|---|---|---|
| Absorbance at 560 nm (water, control) | 0.076 | 0.183 |

Comparison of the degree of color development of the standard solution is shown in Table 3.

TABLE 3

| Example No. | Example 1 | Comparative Example 1 |
|---|---|---|
| Absorbance at 560 nm ($E_{std}$-$E_B$) | 1.267 | 1.271 |

Comparison of changes of the color producing reagents with the lapse of time stored at room temperature is shown in Table 4.

TABLE 4

| Stored time | Example No. | |
|---|---|---|
| | Example 1 | Comparative Example 1 |
| 0 hour | Clear | Clear |
| 18 | Clear | Clouded with a small amount of precipitation |
| 48 | Clear | Clouded with a large amount of precipitation |
| 72 | Clear | Clouded with a large amount of precipitation |

Staining of cuvettes used is compared and shown in Table 5.

TABLE 5

| Example No. | Example 1 | Comparative Example 1 |
|---|---|---|
| Staining | No staining | Whole cuvette was stained light violet |

The degree of staining was obtained by allowing a colored cholesterol standard solution in a glass cuvette to stand for 18 hours at room temperature, removing the solution, washing the cuvette with water and drying the cuvette to observe the degree of staining.

As shown in Tables 1 through 5, the presence of gelatin and β-cyclodextrin do not influence the determined values of cholesterol by the enzymatic method but controls the raise of reagent blank values effectively, stabilizes the color producing reagent and prevents effectively the staining of glass cuvettes by the colored solutions.

EXAMPLE 2

Determination of Free Cholesterol in Serum

A color producing reagent was prepared in the same manner as described in Example 1 except for not using gelation.

Measurement of Free Cholesterol in Serum

The procedures of Example 1 were repeated.
The results are shown in the following Tables 6 to 8.
Comparison of reagent blank values is shown in Table 6.

TABLE 6

| Example No. | Example 1 | Example 2 |
|---|---|---|
| Absorbance at 560 nm (water, control) | 0.076 | 0.081 |

Changes of the color producing reagents with the lapse of time stored at room temperature are shown in Table 7.

TABLE 7

| Stored time | Example No. | |
|---|---|---|
| | Example 1 | Example 2 |
| 0 hour | Clear | Clear |
| 18 | Clear | Clear |
| 48 | Clear | Clear |
| 72 | Clear | Clear |

Staining of cuvettes used is compared and shown in Table 8.

TABLE 8

| Example No. | Example 1 | Example 2 |
|---|---|---|
| Staining | No staining | Whole cuvette was stained light violet |

As is clear from Tables 6 through 8, β-cyclodextrin has effects for effectively control the raise of reagent blank values and for stabilizing the color producing reagents but has no effect for preventing the glass cuvettes from staining.

REFERENCE EXAMPLE 1

Determination of Free Cholesterol in Serum

A color producing reagent was prepared in the same manner as described in Example 1 except for not using β-cyclodextrin.

Measurement of Free Cholesterol in Serum

The procedures of Example 1 were repeated.
The results are shown in the following Tables 9 and 10.
Comparison of reagent blank values is shown in Table 9.

TABLE 9

| Example No. | Example 2 | Reference Example 1 |
|---|---|---|
| Absorbance at 560 nm (water, control) | 0.081 | 0.209 |

Staining of cuvettes used is compared and shown in Table 10.

TABLE 10

| Example No. | Example 2 | Reference Example 1 |
|---|---|---|
| Staining | Whole cuvette was stained light violet | No staining |

As is clear from Tables 9 and 10, gelatin has no effect for controlling the raise of reagent blank values but has an effect for preventing the glass cuvette from staining.

EXAMPLE 3

Determination of Free Cholesterol in Serum

A color producing reagent was prepared in the same manner as described in Example 1 except for using 0.3% of γ-cyclodextrin in place of 0.2% of β-cyclodextrin.

Measurement of Free Cholesterol in Serum

The procedures of Example 1 were repeated.

COMPARATIVE EXAMPLE 2

Determination of Free Cholesterol in Serum

A color producing reagent was prepared in the same manner as described in Example 3 except for not using gelatin and γ-cyclodextrin.

Measurement of Free Cholesterol in Serum

The procedures of Example 1 were repeated.
Comparison between the results obtained in Example 3 and Comparative Example 2 is shown in Tables 11 to 15.
The results of measured values are shown in Table 11.

TABLE 11

| Serum No. | Example No. | |
|---|---|---|
| | Example 3 (mg/dl) | Comparatie Example 2 (mg/dl) |
| 1 | 52.7 | 53.0 |
| 2 | 48.1 | 48.0 |

TABLE 11-continued

| Serum No. | Example No. | |
|---|---|---|
| | Example 3 (mg/dl) | Comparatie Example 2 (mg/dl) |
| Average | 50.4 | 50.5 |

Comparison of reagent blank values is shown in Table 12.

TABLE 12

| | Example No. | |
|---|---|---|
| | Example 3 | Comparative Example 2 |
| Absorbance at 560 nm (water, control) | 0.071 | 0.190 |

Comparison of the degree of color development of the standard solution is shown in Table 13.

TABLE 13

| | Example No. | |
|---|---|---|
| | Example 3 | Comparative Example 2 |
| Absorbance at 560 nm ($E_{std}$-$E_B$) | 1.270 | 1.268 |

Comparison of changes of the color producing reagents with the lapse of time stored at room temperature is shown in Table 14.

TABLE 14

| Stored time | Example No. | |
|---|---|---|
| | Example 3 | Comparative Example 2 |
| 0 hour | Clear | Clear |
| 18 | Clear | Clouded with a small amount of precipitation |
| 48 | Clear | Clouded with a large amount of precipitation |
| 72 | Clear | Clouded with a large amount of precipitation |

Staining of cuvettes used is compared and shown in Table 15.

TABLE 15

| | Example No. | |
|---|---|---|
| | Exanple 3 | Comparative Example 2 |
| Staining | No staining | Whole cuvette was stained light violet. |

EXAMPLE 4

Determination of Free Cholesterol in Serum

A color producing reagent was prepared in the same manner as described in Example 1 except for using a mixture of β-cyclodextrin and γ-cyclodextrin (1:1 by weight) in an amount of 0.2% in place of 0.2% of β-cyclodextrin.

Measurement of Free Cholesterol in Serum

The procedures of Example 1 were repeated.

COMPARATIVE EXAMPLE 3

Determination of Free Cholesterol in Serum

A color producing reagent was prepared in the same manner as described in Example 4 except for not using gelatin and the mixture of β-cyclodextrin and γ-cyclodextrin.

Measurement of Free Cholesterol in Serum

The procedures of Example 1 were repeated.
Comparison between the results obtained in Example 4 and Comparative Example 3 is shown in Table 16 to 20.
The results of measured values are shown in Table 16.

TABLE 16

| Serum No. | Example 4 (mg/dl) | Comparative Example 3 (mg/dl) |
| --- | --- | --- |
| 1 | 60.5 | 61.1 |
| 2 | 48.9 | 48.3 |
| 3 | 55.2 | 54.7 |
| 4 | 35.5 | 36.1 |
| 5 | 42.6 | 42.3 |
| Average | 48.54 | 48.50 |

Comparison of reagent blank values is shown in Table 17.

TABLE 17

| | Example 4 | Comparative Example 3 |
| --- | --- | --- |
| Absorbance at 560 nm (water, control) | 0.075 | 0.196 |

Comparison of the degree of color development of the standard solution is shown in Table 18.

TABLE 18

| | Example 4 | Comparative Example 3 |
| --- | --- | --- |
| Absorbance at 560 nm ($E_{std}$-$E_B$) | 1.283 | 1.277 |

Comparison of changes of the color producing reagents with the lapse of time stored at room temperature is shown in Table 19.

TABLE 19

| Stored time | Example 4 | Comparative Example 3 |
| --- | --- | --- |
| 0 hour | Clear | Clear |
| 18 | Clear | Clouded with a small amount of precipitation |
| 48 | Clear | Clouded with a large amount of precipitation |
| 72 | Clear | Clouded with a large amount of precipitation |

Staining of cuvettes used is compared and shown in Table 20.

TABLE 20

| | Example 4 | Comparative Example 3 |
| --- | --- | --- |
| Staining | No staining | Whole cuvette was stained light violet. |

EXAMPLE 5

Measurement of Activity of Superoxide Dismutase (SOD) in Serum

A first reagent:
| | |
| --- | --- |
| 0.1 M phosphate buffer | pH 8.0 |
| $NO_2$—TB | 200 mg/l |
| Xanthine | 0.4 mmole/l |
| EDTA · 2Na | 0.005% |
| Triton X-100 | 0.1% |
| β-cyclodextrin | 0.2% |

A second reagent:
| | |
| --- | --- |
| 0.1 M phosphate buffer | pH 8.0 |
| Xanthine oxidase | 150 units/l |
| EDTA · 2Na | 0.005% |

Reaction stopper:
0.1 N HCl solution containing 0.1% of Triton X-100

Measurement of Activity of SOD

To 100 μl of serum, 1 ml of the first reagent was added and heated at 37° C. for 3 minutes. Then, 0.1 ml of the second reagent was added thereto and incubated at 37° C. for 20 minutes. Subsequently 3 ml of the reaction stopper was added to the incubated solution. Absorbance ($E_S$) at the wavelength of 560 nm was measured using reagent blank as control. The reagent blank was prepared by adding 1 ml of the first reagent to 100 μl of deionized water, heating at 37° C. for 20 minutes, adding 3 ml of the reaction stopper, and adding 0.1 ml of the second reagent thereto.

Absorbance ($E_B$) was obtained by repeating the same procedure as done in the case of serum by using deionized water in place of serum.

The activity of SOD can be represented by the damaging rate calculated by the following equation:

$$\text{damaging rate } (\%) = \frac{E_B - E_S}{E_B} \times 100$$

COMPARATIVE EXAMPLE 4

Measurement of Activity of SOD

A first reagent:
Prepared in the same manner as described in Example 5 except for not using β-cyclodextrin.

A second reagent:
The same as used in Example 5.

Measurement of activity of SOD:
The procedures described in Example 5 were repeated and the damaging rate (%) was measured.

Comparison of storage stability of the first reagents:
The degree of coloring when the first reagents were stored at room temperature (20° to 25° C.) was measured at the wavelength of 560 nm using water as control.

The results are as shown in Table 21.

TABLE 21

| Storage days | Example 5 | Comparative Example 4 |
| --- | --- | --- |
| 0 day | 0.010 | 0.010 |
| 1 | 0.010 | 0.035 |
| 2 | 0.010 | 0.071 |
| 3 | 0.010 | 0.125 |
| 4 | 0.010 | 0.168 |

As is clear from Table 21, no change is admitted in the case of Example 5, but the coloring, that is, the absorbance increases gradually in the case of Comparative Example 4 with the lapse of time due to the decomposition of $NO_2$—TB.

The results of SOD activities measured in Example 5 and Comparative Example 4 are shown in Table 22.

TABLE 22

| Serum No. | Example 5 | Comparative Example 4 |
|---|---|---|
| 1 | 12.1 | 11.9 |
| 2 | 4.6 | 4.6 |
| 3 | 10.5 | 11.0 |
| 4 | 14.9 | 15.2 |
| 5 | 2.3 | 2.0 |
| 6 | 9.8 | 10.1 |
| 7 | 6.6 | 6.9 |
| 8 | 4.2 | 4.0 |
| 9 | 3.3 | 3.2 |
| 10 | 14.4 | 14.1 |
| Average | 8.27 | 8.30 |

As shown in Table 22, there is admitted no significant difference in measured values between Example 5 and Comparative Example 4.

EXAMPLE 6

Determination of Free Cholesterol in Serum

A color producing reagent was prepared in the same manner as described in Example 1 except for using heptakis(2,6-di-o-methyl)-β-cyclodextrin in a concentration of 2% in place of β-cyclodextrin.

Measurement of Free Cholesterol in Serum

The procedures of Example 1 were repeated.

The results were the same as those obtained in Example 1.

EXAMPLE 7

Measurement of Activity of SOD in Serum

A first reagent:

A first reagent was prepared in the same manner as described in Example 5 except for using heptakis(2,3,6-tri-o-methyl)-β-cyclodextrin in a concentration of 3% in place of β-cyclodextrin.

A second reagent:

The same as that used in Example 5.

Reaction stopper:

The same as that used in Example 5.

Measurement of activity of SOD:

The procedures of Example 5 were repeated.

The results were the same as those obtained in Example 5.

What is claimed is:

1. In a process for stabilizing a tetrazolium salt used as a color indicator in the determination of a substrate which is an oxidizable biochemical material by oxidizing said substrate with an oxidase, wherein said tetrazolium salt is selected from the group consisting of compounds of the formulas II, III, and IV:

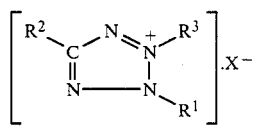
(II)

wherein X is halogen; and each of $R^1$, $R^2$ and $R^3$ is independently an organic residue selected from the group consisting of phenyl, phenyl substituted with at least one halogen, nitro and

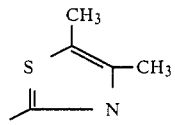
(III)

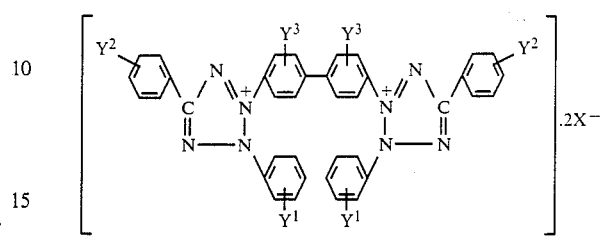

wherein each of $Y^1$ and $Y^2$ is independently —$NO_2$ or —H; $Y^3$ is —$OCH_3$, —I or —H; and X is a halogen;

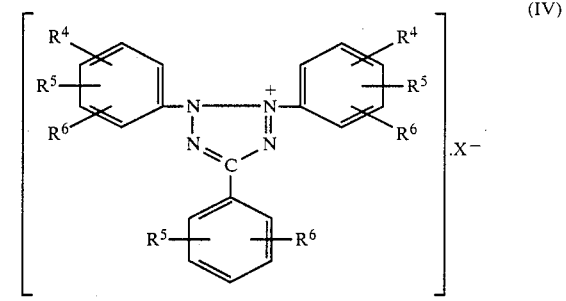
(IV)

wherein each R4 is nitro or halogen, provided that at least one $R^4$ is nitro; $R^5$ is hydrogen; a lower alkyl group, a lower alkoxy group or a halogen; $R^6$ is hydrogen or —$OR^7$; $R^7$ is a straight- or branched-chain aliphatic hydrocarbon having 1 to 4 carbon atoms which has at least one functional group selected from the group consisting of sulfonic acid, sulfonic acid salt, carboxyl, and carboxyl salt, and can also have a hydroxyl group, provided that the sum of the number of sulfonic acid group, sulfonic acid salt group, carboxyl group, and carboxyl salt group contained in $R^6$ is 2 or more and one of said functional groups forms an intramolecular salt with a tetrazolium ring; and X is a halogen, the improvement wherein said tetrazolium salt is stabilized against chemical decomposition by adding to an aqueous solution of said tetrazolium salt at least one member selected from the group consisting of:

(i) β-cyclodextrin;

(ii) a derivative of β-cyclodextrin represented by the formula:

(V)

wherein CD is a cyclodextrin residue, $Z^1$ is —$NO_2$, —$PO_3H$, —$SO_3H$ or a group of the formula —$(CH_2)_nZ^2$; $Z^2$ is —$SO_3H$ or —$CO_2H$; n is an integer of 1 to 4; and m is a positive number having a value of 1 to 5, or represented by the formula:

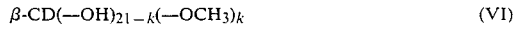
(VI)

wherein k is a positive number having a value of 1 to 21; and (iii) γ-cyclodextrin.

2. The process of claim 1, wherein the concentration of β-cyclodextrin in the aqueous solution of the tetrazolium salt is 0.01 to 1.5 weight/volume percent.

3. The process of claim 1, wherein the concentration of γ-cyclodextrin in the aqueous solution of the tetrazolium compound is 0.01 to 10 weight/volume percent.

4. The process of claim 1, wherein the concentration of the derivative of β-cyclodextrin in the aqueous solution of the tetrazolium salt is 0.01 to 10 weight/volume percent.

5. The process of claim 1, wherein a mixture of β-cyclodextrin and γ-cyclodextrin is used for stabilizing the tetrazolium salt, the concentration of β-cyclodextrin in the aqueous solution of the tetrazolium salt being 0.01 to 1.5 weight/volume percent, and the concentration of γ-cyclodextrin in said aqueous solution being 0.01 to 10 weight/volume percent.

6. The process of claim 1, wherein a mixture of the derivative of β-cyclodextrin and γ-cyclodextrin is used for stabilizing the tetrazolium salt, the concentration of the derivative of β-cyclodextrin in the aqueous solution of the tetrazolium salt being 0.01 to 10 weight/volume percent, and the concentration of γ-cyclodextrin in said aqueous solution being 0.01 to 10 weight/volume percent.

* * * * *